United States Patent [19]

Davison

[11] Patent Number: 4,983,721

[45] Date of Patent: Jan. 8, 1991

[54] SOLVENTS FOR COLLAGEN

[75] Inventor: Peter F. Davison, Lexington, Mass.

[73] Assignee: Boston Biomedical Research Institute, Boston, Mass.

[21] Appl. No.: 276,285

[22] Filed: Nov. 25, 1988

[51] Int. Cl.$^5$ .................... A61K 37/12; C07K 15/20; C08H 1/06

[52] U.S. Cl. .................................................. 530/356

[58] Field of Search .......................... 530/356; 514/21

[56] References Cited

PUBLICATIONS

Gross et al., PNAS, vol. 41, No. 1, 1/15/55, pp. 1–7.

Nimni et al., Biochem. Biophys. Research Comm. 25: 434–440 (1966).

Primary Examiner—Howard E. Schain
Assistant Examiner—Choon Koh
Attorney, Agent, or Firm—Hamilton, Brook, Smith & Reynolds

[57] ABSTRACT

A method for extracting collagen from animal collagen-containing tissue using a solution of an organic amine salt. The collagen product has many uses such as cell growth matrices, prosthetic devices, synthetic skin, dressings for wounds, or membranes.

22 Claims, 6 Drawing Sheets

SOLVENTS FOR COLLAGEN

GOVERNMENT SUPPORT

The work described herein was supported by one or more grants from the National Institutes for Health.

BACKGROUND

Collagen is a fibrous protein having a very high tensile strength which can be found in all multicellular organisms. The purpose of collagen is to hold cells and tissues together and to direct the development of mature tissue. Collagen is the major fibrous protein in skin, cartilage, bone, tendon, blood vessels and teeth.

There are many types of collagen which differ from each other to meet the requirements of various tissues. Some examples of types of collagen are as follows: type one $[\alpha 1(I)]_2 \alpha 2$ which is found in the skin, tendon, bone and cornea; type two $[\alpha 1(II)]_3$ which is found in the cartilage, intervertebral disc, and vitreous body; type three $[\alpha 1(III)]_3$ which can be found in skin and the cardiovascular system ; type four $[\alpha 1(IV)]_2 \alpha 2(IV)$ which can be found in basement membrane; type five $[\alpha 1(V)]_2 \alpha 2(V)$ and $\alpha/(V)\alpha 2(V)\alpha 3(V)$ which is found in the placenta and skin. Examples of newly identified forms of collagen include type seven (VII) which is found in anchoring fibrils beneath many epithelia; and types nine (IX) and ten (X) which are constituents of cartilage.

The chemical characterization of collagen was difficult since its low solubility made isolation of collagen a tedious task. Eventually, it was discovered that collagen from tissues of young animals was not as extensively crosslinked as that of mature tissues and thus was more amenable to extraction. For example, the basic structural unit of type I collagen, tropo-collagen, can be extracted in intact form from young collagen-containing tissues.

The extraction of collagen from collagen-containing tissues is of interest since collagen is useful as a support gel for cell growth or as a matrix suitable for shaping into prosthetic devices and synthetic skin or membranes. Presently, salt solutions are being used to extract the salt soluble fractions of collagen which is a small fraction with minimal crosslinking. Dilute acid solutions are also being used (i.e., acetic, citric, formic, and hydrochloric acids) to extract collagen from young rapidly growing tissues. The acid-soluble fraction is slightly greater than the salt-soluble fraction; however, in some instances, the extraction solutions may be more dangerous to handle due to their acidic pH. See Gross et al., *Proc. Natl. Acad. Sci USA*, 41, pp 1–7, (1955) and Davison et al, *Conn. Tiss. Res.*, 1, pp 205–216, (1972).

Nimni et al., *Biochemical and Biophysical Research Communications*, Vol. 25, No. 4, pp 434–440 (1966) teach the extraction of collagen from the skin of rats using penicillamine and cysteamine in a NaCl solution. Both penicillamine and cysteamine are very expensive solvents which have not been widely used. The extraction method of Nimni et al. uses penicillamine or cysteamine to disrupt the crosslinks prior to extracting with a sodium chloride solution. Nimni et al. does not teach the regeneration of collagen after extraction.

SUMMARY OF THE INVENTION

The invention described herein is a method for extracting collagen from animal collagen-containing tissue comprising contacting the tissue with a solution of an organic amine salt wherein said organic amine is selected from the group consisting of diamines and aminoalcohols, and thereafter forming a gel from said collagen extracted from animal collagen-containing tissue.

The extraction process of the present invention has advantages over the processes presently employed. It can be conducted at a neutral pH thereby eliminating risks derived from handling acidic solutions. The viscosity of the collagen is not as concentration dependent as the salt and dilute acid extraction processes. It is difficult to work with high concentrations of collagen using the salt and dilute acid extraction processes because the viscosity of the collagen product increases with concentration and reaches a point where it is gel-like. This is not the case with the extraction process of the present invention since viscosity concentration dependency is greatly diminished using salts of organic amines.

The invention further encompasses the collagen prepared using the above method and methods of using the collagen product such as in prosthetic devices and cell growth matrices. The collagen can also be used as a dressing for a burn or a wound, synthetic skin, or sheathing for repairing ruptured tendons. Collagen prepared according to the present method restricts bacteria from a burn or wound and therefore aids in healing.

DETAILED DESCRIPTION

Figure 1A:
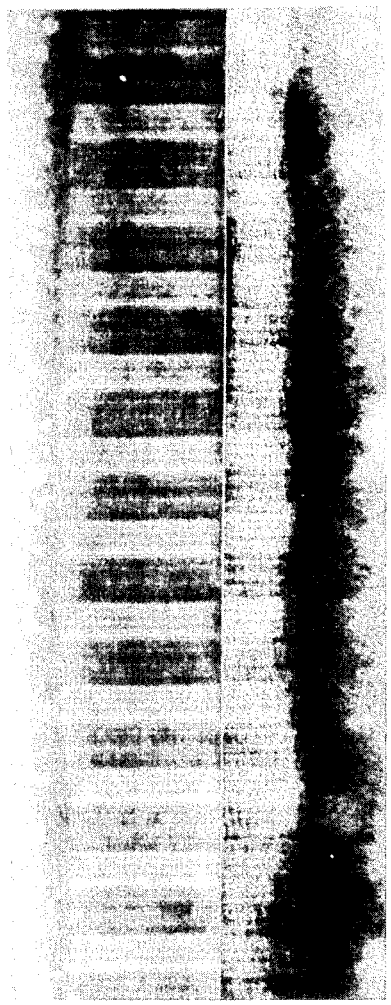
FIG. 1a is an electron micrograph of rat tendon fibrils regenerated from ethylenediamine hydrochloride (hereinafter ED hydrochloride) soluble collagen by dilution with water.

The collagen of the present invention can be of any type and can be extracted from any collagen-containing animal tissue. Examples of possible collagen containing tissues are tendon, skin, cornea, bone, cartilage intervertebral disc, fetal skin, cardiovascular system, basement membrane, placenta, and anchoring fibrils beneath any epithelia.

The solution of organic amine salt used as an extractant can be any salt of an organic amine selected from the group consisting of diamines and aminoalcohols. Examples of such organic amines are methylenediamine, ethylenediamine, propylenediamine, butylenediamine, pentylenediamine hexadiamine heptadiamine, octadiamine, aminomethanol, 2-aminoethanol, aminoethanol, aminopropanol aminobutanol, aminopentanol, aminohexanol, aminoheptanol, aminooctanol. The preferred organic amines are ethylenediamine, propylenediamine hexadiamine, and 2-aminoethanol.

Any salt of a strong acid can be used in the present invention. Examples of salts which are useful within the organic amine salt solution are hydrochlorides, hydrofluorides, and hydrobromides. The preferred salt is hydrochloride.

Conditions whereby collagen is extracted are those where the pH of the organic amine salt solution is about neutral, preferably about 6.0 to about 9.0, most preferably about 7.6 to about 8.2. The extraction process of the present invention can be conducted at a temperature from about 3° C. to about 35° C., preferably about 4° C. At temperatures above 35° C., the collagen begins to denature. Concentrations of the organic amine salt which are useful within the present invention are from about 0.3 to about 2.0 moles per liter of solution, preferably about 1.0 moles per liter of solution. The collagen-containing animal tissues can be soaked in the organic amine salt solution for at least several hours, or preferably overnight. The soaked collagen-containing animal tissue may then be subjected to shearing forces to obtain a uniform slurry.

Shearing force can be applied by a great variety of techniques to be useful for the present invention. Examples of such shearing forces are blending, milling and homogenization. The preferred shearing force is homogenization. The soaked tissues optionally can be sheared one or several times.

A thiol reagent can be added to the collagen containing mammalian tissue to aid in breaking disulfide bonds making the collagen more soluble in the extractant. The thiol reagent is especially useful for type IV collagen. Thiols which can be used are mercaptoethanol, mercaptopropanol, merceptobutanol, mercaptopentanol, mercaptohexanol mercaptoheptanol, mercaptooctanol, mercaptononanol, and dithiothreitol, and dithioerythreitol. The preferred thiols are mercaptoethanol and dithiothreitol. The thiol reagent can be added at any point in the method; however, preferably it is added after the first shearing step prior to subsequent shearing steps to minimize oxidation of the thiol.

The present method may also include a separation step subsequent to the homogenization steps. The separation step could be one or more of centrifugation, distillation, dilution, or dialysis. The preferred separation steps are centrifugation followed by dialysis.

The method can also include a step wherein the extracted collagen is regenerated. This can be done by extrusion, casting, or molding a concentrated solution of extracted collagen in an organic amine salt solution. Extrusion can be through an opening or openings of a desired shape into a buffer solution wherein the collagen takes on the desired shape. The shape can be any shape which regenerates collagen in a form which is desired. Examples of such shape are circular whereby a cylinder is formed which could be useful for fabricating prosthetic devices. The shape could be very small holes such as those found in a jet, syringe or porous membrane. This particular shape would form threadlike, fibrillar collagen (thread-like structures) which are useful for forming mats of collagen for cell growth matrices, synthetic skins or dressings, for example. A substantial amount of organic amine solvent is removed prior to casting or molding the extracted collagen. The extracted collagen can be cast or molded into desired shapes such as threads, cylinders or blocks, for example.

This invention will now be more specifically described by the following examples.

EXAMPLE 1

Ethylenediamine, propylenediamine, hexanediamine and 2-aminoethanol were purchased from Aldrich Chemical or Fluka Chemical Corporations. The diluted reagents were neutralized with concentrated hydrochloric acid to a pH between 7.5 and 9.5, preferably 7.6 to 8.2. The collagen from 6.12 week rat tail tendons, rabbit and bovine foot tendons. corneas and placentas was studied. Rat tendons were cleanly dissected from the tail that was iced, skinned, and briefly washed with 1.0 mM benzamidine hydrochloride and 5.0 mM ethylenediaminetetraacetic acid (EDTA) in 0.1 M NaCl to inhibit proteolysis as described in Davison, P. F., *Conn. Tiss. Res.* (1988). Bovine eyes obtained from an abattoir were washed and bisected. The corneas were cut out from the anterior segment and were scraped to remove the epithelium, endothelium and Descemet's membrane. Bovine placentas, also from an abbatoir, were dissected from 6-month or older fetuses Extensor tendons were cut from calf fore hocks or rabbit rear feet. The tendons, placental membranes and corneas were washed for 30 minutes in iced solutions of the protease inhibitor and were frozen on dry ice and then powdered in liquid nitrogen in a Wiley mill. The tissues or tissue powders were soaked overnight at 4° C. in 1.0M ethylenediamine hydrochloride (pH 8), or hydrochloride salts of the other solvents, and then sheared through a Dounce homogenizer several times to obtain a uniform slurry. Optionally, mercaptoethanol was added at this time and tissues were stirred for 24 hours before a second homogenization with the Dounce homogenizer and centrifugation at 36,000 g for 40 minutes or 83,000 g for 1 hour in a Beckman SW 28 Ti rotor. The clear supernatant was decanted, the viscous residue was redispersed in fresh solvent, and the extraction process was repeated two or three times. The yield of dissolved collagen diminished in successive extracts.

Optionally, the insoluble, viscous residue was dialyzed to 0.2 M acetic acid with several changes of dialyzate. Pepsin was then added to the slurry in an amount of 1% by weight of the collagen, and the slurry was stirred overnight at 4° C. The resulting digests were diluted with 10% by volume 1M NaCl and the pepsin-soluble and pepsin-insoluble fractions were separated by centrifugation. Gel electrophoresis was carried out as described in Davison, P. F., *J. Biol. Chem.*, 253:5635-5646, (1978). The Coomassie blue-stained gels were scanned with a Joyce-Loebl Ephortec densitometer.

To estimate the denaturation temperature, the viscosities of the collagen solutions were measured in a Cannon viscometer and in a falling-ball viscometer (Gilmont) in a water bath. The temperature was progressively raised at 5 minute intervals. Sedimentation studies were conducted in a Beckman Model E centrifuge equipped with Rayleigh Optics. A polarized helium-neon laser light source was used in continuous mode. Rayleigh interferograms on Kodak 2415 film were read at 35 micron intervals using an automated plate reader. Fringe displacements were obtained using a Fourier analysis method. Fringe displacement data were analyzed on an Apple Macintosh-II microcomputer with ZBasic computer programs to smooth and differentiate the profiles of refractive increment versus cell radius.

For amino acid analysis, the dried proteins were hydrolyzed in HCl vapor and the phenylthiohydantoin derivatives of the amino-acids were resolved by the Waters Pico-tag system. Hydroxyproline was measured in acid hydrolyzates of tissue fractions by the method of Jamall et al., *Anal. Biochem.*, 112:70-75 (1981). The $^3$H-borohydride-reducible residues in the collagen dissolved in 1M ethylenediamine solutions were examined after acid and alkaline hydrolysis by column chromatography. The electron microscope used was a Philips EM 300.

When lyophilized, acid-soluble or pepsin-solubilized collagens (types I, III, and V) from rat, rabbit, and bovine tissues were stirred with 0.5-1.0M ethylenediamine hydrochloride solutions at pH 7-8.5, the collagens dissolved to yield viscous solutions. Dissolution was more rapid in the 1M solution. After 24 hour stirring, the suspensions were centrifuged at 36,000 g to give clear viscous supernatant solutions. The supernatant solution was centrifuged at a high speed (83,000 g) sedimenting gel-like fractions and a less viscous supernatant. When analyzed by discontinuous gel electrophoresis, the component polypeptide chains in both gel and supernatant did not seem distinguishable. On the basis of ultracentrifuge data, it was concluded that the gel fraction contains aggregates built from apparently similar ratios of collagen α-chains and crosslinked chains as the presumptive monomeric components in the high-speed supernatant. Neutralized 1M salt solutions of propylenediamine and 2-aminoethanol have similar solvent properties for collagen as ED hydrochloride. 1, 6-diaminohexane hydrochloride was a less effective solvent.

Figure 1B:
FIG. 1b is an electron micrograph of a section from a mat of reconstituted collagen fibrils formed by diluting an ED hydrochloride extract of rat-tail tendon with water.
Figure 3:
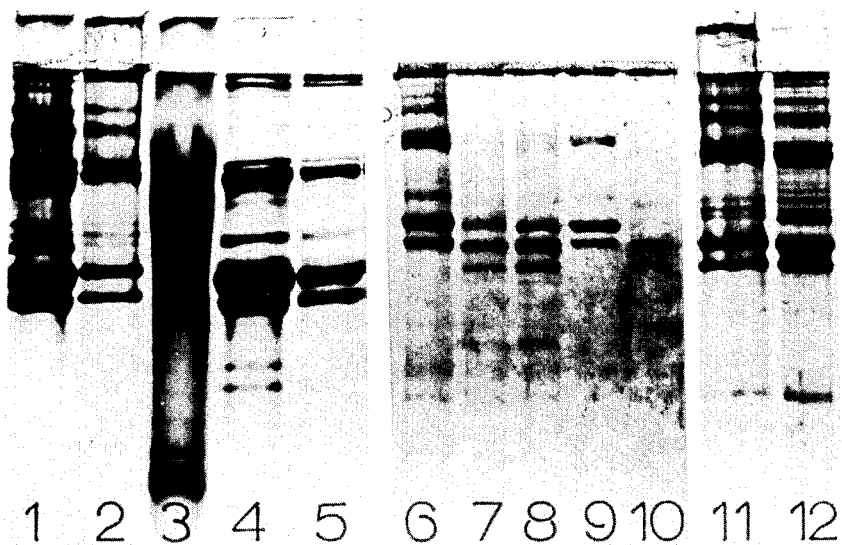
FIG. 3 is a photograph of an SDS-polyacrylamide (6–10%) gradient gel stained with Coomassie Blue wherein the samples are as follows: (1) 20 ug of ED hydrochloride extracted, water-insoluble proteins from calf corneas; (2) 60 ug of ED hydrochloride extracted, water-insoluble proteins from calf corneas; (3) the water-soluble components from the ED hydrochloride extracted proteins from calf corneas; (4) 20 ug of ED hydrochloride extracted, water insoluble proteins from calf corneas after treatment with pepsin; (5) 60 ug of ED hydrochloride extracted, water insoluble proteins (from calf corneas) after treatment with pepsin; (6) ED hydrochloride-extracted, water-insoluble, calf corneal proteins; (7) ED hydrochloride-extracted, water insoluble calf corneal proteins digested for 16 hours at 20° C. with 2.0 ug/ml of collagenase; (8) ED hydrochloride-extracted, water insoluble calf corneal proteins digested for 16 hours at 20° C. with 1.0 ug/ml of collagenase; (9) ED hydrochloride extracted, water insoluble calf corneal proteins digested for 16 hours at 20° C. with 0.5 ug/ml of collagenase; and (10) ED hydrochloride-extracted, water insoluble calf corneal proteins digested for 16 hours at 20° C. with 10 ug/ml of collagenase.
Figure 4B:
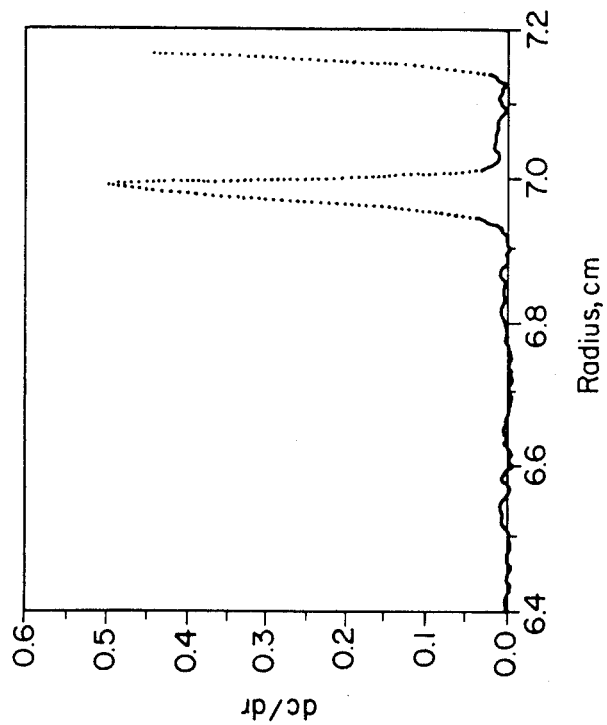
FIG. 4 is a graph of the concentration profiles of the sedimenting boundaries for a 0.5M ED hydrochloride solution of rat tendon collagen previously clarified at 28,000 g for forty minutes (A) and previously clarified at 84,000 g for one hour (B).
Figure 4A:
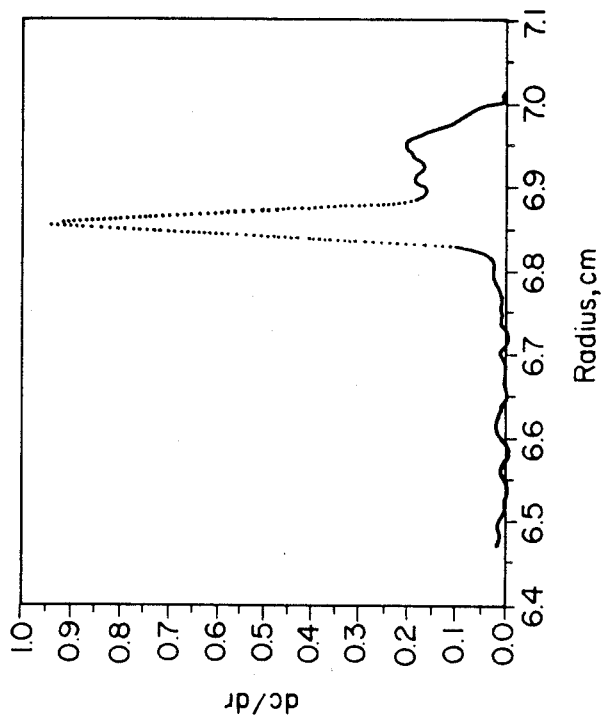

The type 1 collagen solutions are stable in ED hydrochloride salt solutions to dilutions down to approximately 0.2-0.3M. When further diluted or dialyzed to water the collagen formed a gel, a fibrous aggregate, or from dilute solutions (less than 0.2 mg/ml) a fine precipitate. In ED hydrochloride concentrations of 0.05M and below, essentially all of type I, II, III, and pepsin-solubilized V collagens precipitated on standing (FIG. 3). A fine precipitate prepared from rat tendon collagen, when examined by electron microscopy, demonstrated a well defined native type band pattern as seen in FIG. 1. At higher concentrations of collagen, the precipitates formed a gel. Soft gels readily coacervated on stirring, but more concentrated gels formed tough, elastic masses after dialysis to water. Pepsin-treated type I collagen, when precipitated by dilution of 1M ED hydrochloride solutions also formed a gel, but the stained fibrils examined in the electron microscope showed a band pattern much less regular than that in native collagen fibrils.

EXAMPLE 2

The solubility of collagen in ED hydrochloride from that in acid solutions. In dilute acetic acid, type I collagen is soluble only at low salt concentrations. If the solution is neutralized, the solubility is greater in high salt concentrations and in the presence of some bivalent ions (particularly calcium). The solubility is also temperature dependent. Collagen shows the following behavior in ED salt solutions:

1. No collagen precipitated when rat, rabbit, or bovine type I collagen dissolved in 1M ED hydrochloride was mixed with an equal volume of 5M NaCl. All the collagen precipitated when mixed with an equal volume of saturated ammonium sulfate. No collagen precipitated when collagen in 1M ED hydrochloride was acidified with glacial acetic acid.

2. Solutions of 2-4 mg/ml of collagen in 1M ED hydrochloride diluted 20-fold with water at room temperature formed fine fibrous precipitates which were particularly apparent when the solution was stirred. The collagen formed a firm gel when it was diluted with cold water over several hours. Stirring of this gel caused coacervation and aggregation of fibrils.

3. Solutions of 0.1-1 mg/ml of collagen in 1M ED hydrochloride dialyzed to a 0.1M NaCl solution at 4° C. gave a fibrous precipitate. No precipitate formed at 4° C. when the same collagen was dialyzed to a 0.3M or 1.0M NaCl solution. A gel was formed when either of these solutions were warmed. The gel formed upon warming of the 1M NaCl solution, redissolved on cooling to 4° C.

4. No precipication occurred at a pH of 5.5 when 1.2 mg/ml collagen in 1M ED hydrochloride solutions were dialyzed with 40 volumes of 0.1M buffers. At higher pH's, fibrous precipitates formed faster at pH of 8 than at a pH of 7. Precipitates formed faster with borate buffers than with phosphate buffers. No collagen precipitated when the solutions were dialyzed to 1M ammonium hydroxide.

5. Concentrated solutions of collagens in ED hydrochloride solutions can be extruded through a jet or syringe into water or buffer solutions to regenerate fibrillar collagen in the form of a thread.

The nature of the collagen precipitates in organic amine salt solutions can be controlled in ways not available when gels are formed by neutralizing acid solutions of collagen and then gently warming them. It is clear that temperature, pH, ionic strength, and salt composition can effect the manner in which collagen precipitates from solution. Furthermore, mixtures of collagen types can be coprecipitated by dilution or dialysis.

EXAMPLE 3

Regenerated fibrils of type I collagen in the form of gels or fine precipitates were filtered on Nucleopore or Millipore 2 um filters and dried to form a thin, tough mat (FIG. 1) Several mats were well washed in buffered saline, sterilized by ultraviolet radiation and seeded with rabbit or human skin fibroblasts. The cells grew over the surface of the matrix when cultured with Dulbecco's modified Eagle's medium with 10% serum. The fibrils in such gels were mostly 60,200 nm in diameter. The fibrils produced from neutralized and warmed acid-extracted collagen were thicker (150–400 nm). The latter gels were almost transparent, the former were opaque.

The soluble collagen was slowly extracted when finely divided tissues such as tendon and cornea were homogenized with neutral 1M ED hydrochloride with or without 2mM mercaptoethanol. Studies with aliquots of tail tendons from 6-week old rats showed that a similar yield of soluble collagen was obtained with either 0.2M acetic acid or with 1.0M ED hydrochloride. Approximately 95% of the tendon collagen was dissolved and 5% remained undissolved. Dialysis of the ED hydrochloride extract against water caused the collagen to precipitate. The collagen remaining in solution was recovered by freeze-drying. Half of the fraction of the tendon insoluble in 1M ED hydrochloride could be solubilized by treatment with pepsin. At least 95% of the pepsin-solubilized protein was type I collagen. The hydroxyproline content of the small, pepsin-insoluble residue was negligible implying that less than 1% of the tendon collagen could not be solubilized. Thus 1M ED hydrochloride dissolves the preponderant fraction of young rat tendon collagen.

In a preparation from calf cornea, soluble collagen that amounted to 20–30% of the tissue dry weight was obtained in three successive 1M ED hydrochloride extracts after 24 hours stirring and homogenization. The collagen was recovered by dialyzing the extracts to water and centrifuging the resulting suspension to obtain the precipitated collagen. Dialysis and lyophilization of the supernatant from this centrifugation yielded a significant fraction of water-soluble proteins and proteoglycans. Finally, the residue of material insoluble in 1M ED hydrochloride was dialyzed to 0 2 M acetic acid and the resulting gel was digested with pepsin over 24 hour at 4° C. A volume of 1M sodium chloride equal to one-tenth of the total volume was added to this solution and the solution was centrifuged. The insoluble residue was dialyzed against water and lyophilized. The solubilized collagen was precipitated, redissolved in acetic acid, dialyzed free of salt, and lyophilized. The yields from a typical corneal preparation were: ED hydrochloride-soluble, 23%; pepsin-soluble collagen 55%; insoluble material, 2%; and soluble extract of unidentified proteins and proteoglycans, 20%.

Finely divided, milled powders from the scraped stroma of five corneas from adult cattle were similarly treated with 1M ED hydrochloride. The dispersed particles swelled very little. This observation may be generalized with other observations on tendons to conclude that ED hydrochloride, like acid solvents, can extract less soluble collagen from tissues of older animals.

EXAMPLE 5

The extraction process with ethylenediamine is greatly promoted by homogenization or shearing forces Thus an overnight dispersion of milled calf extensor tendons or chopped rat tail tendons in 1M ED hydrochloride swelled very little and resembled a slurry of cellulose powder. Two passes in a Dounce homogenizer transformed the slurry into a highly viscous gel.

Figure 2A:
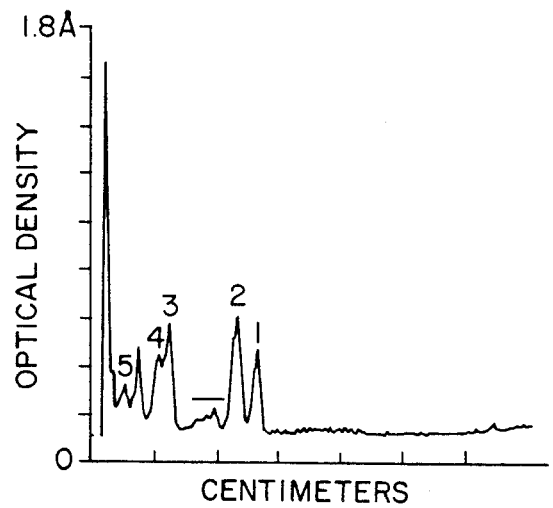
FIG. 2 is a graph of the densitometer traces from Coomassie-Blue-stained SDS-polyacrylamide gels after electrophoresis of (a) the material precipitated by dialyzing to water an ED hydrochloride extract from calf corneas and (b) a similar fraction extracted from calf corneas by propylenediamine hydrochloride.
Figure 2B:
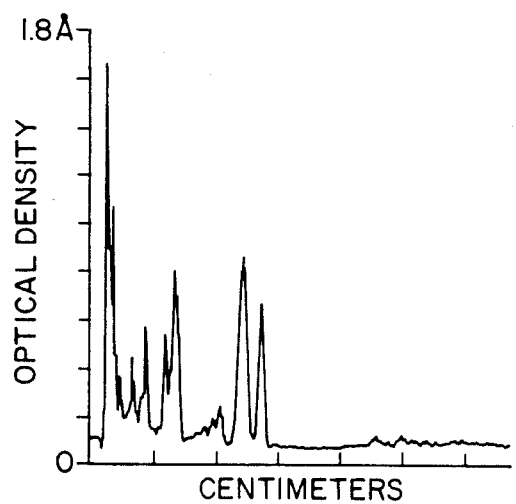
Figure 2C:
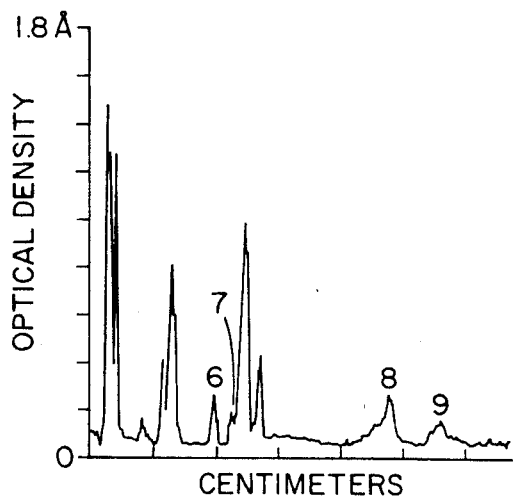

The electrophoretic behavior of these ethylene-diamine hydrochloride extracts of different tissues and of the pepsin-solubilized residues is shown in FIGS. 2 and 3. These figures demonstrate that: some protein bands that appear in the ED hydrochloride extract are present in ratios that are changed if mercaptoethanol or dithiothreitol is added to the sample before electrophoresis; ED hydrochloride extraction can selectively dissolve from the tissues certain fractions of the collagen populations that can be tentatively recognized by their electrophoretic mobilities; negligible quantities of types I, III, V, and VI collagens fail to be precipitated by dialysis of the ED hydrochloride extracts to water; and a number of other identified tissue components are extracted by ED hydrochloride, remain soluble when dialyzed to water and can be recovered by lyophilization. Among these components are some with the electrophoretic characteristics of the proteoglycans identified in cornea.

Samples of these ED hydrochloride extracts from tendons and corneas were dialyzed to 0.1M Tris pH 7.6. 0.05M calcium chloride and digested with various ratios of type III collagenase (Advance Biofactures Corp., form III) for 24 hours at 20° C. These digests were dialyzed to 0.05M acetic acid and applied to an electrophoresis gel. The results are shown in FIG. 3. These experiments demonstrate that most of the proteins that were dissolved by ED hydrochloride from the collagen-containing tissues, and that precipitate on dialysis to water, are susceptible to collagenase. At present, it cannot be presumed that this solubility behavior can be used to identify all types of soluble collagens, but it does provide a simple procedure for the selective extraction and enrichment of those fractions of several types of collagen that are not stably and extensively crosslinked.

EXAMPLE 6

Properties of Ethylenediamine Hydrochloride Solutions of Collagen

Type I collagen preparations extracted with 1M ED hydrochloride from rat tendon and clarified at 35,000 g yielded clear solutions whose properties were studied. These solutions were applied to a gel filtration column of Toyo Pearl silica (TSK HW 65S, Supelco) and eluted with 0.5M ED hydrochloride The eluted fractions were dialyzed to water and compared by SDS-polyacrylamide gel electrophoresis. The first fractions contained α-chains and more slowly migrating components including presumptive polymers so large that they did not penetrate the running gel. These polymers were depleted in successive fractions. Thus, aggregates of collagen molecules are dissolved by ED hydrochloride and can be resolved from monomers by this filtration medium.

The type I collagen solutions were also studied by ultracentrifugation. ED hydrochloride extracts from tendon (clarified at 36,000 g) showed that the collagen was heterogeneous, but the extracts clarified at 83,000 g showed a monodisperse sedimenting species with sedimentation velocity of 1.76 S. This value is not extrapolated to zero concentration. The partial specific volume of collagen dissolved in ethylene-diamine hydrochloride has not been determined, so a value of v=0.67 was assumed.

Figure 5:
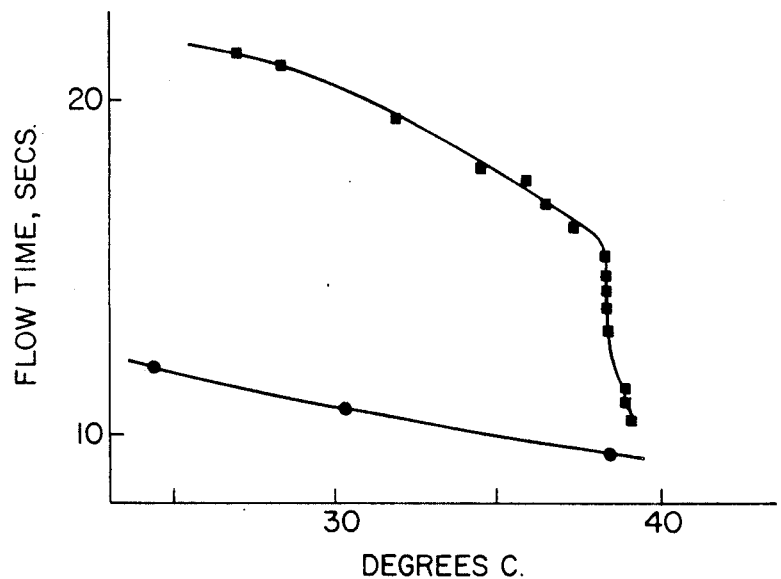
FIG. 5 is a graph which depicts the temperature dependence of the viscosity of a collagen solution (0.64 ug/ml) in 0.5M ED hydrochloride in a falling ball viscometer.

The viscosities of the solutions of collagen in 1M ED hydrochloride were measured in a falling ball viscometer. The results of such measurements on rat tail tendon collagen in 0.5M ED hydrochloride at successively higher temperature (FIG. 5) showed that the denaturation temperature was approximately 38° C. The intrinsic viscosity of the native type I collagen was 17.5 dl/gm, uncorrected to zero concentration or zero shear. The non-Newtonian behavior of collagen in $0.1 \propto 1M$ ED hydrochloride is much less than that observed in acidic or basic solutions (e.g., 0.2M acetic acid 0.11 M NaCl)

All of the collagen solutions were stable when stored for months at 4° C. in 1M ED hydrochloride. No sign of proteolytic attack or growth of microorganisms was found.

Those skilled in the art will know, or be able to ascertain using no more than routine experimentation many equivalents to the specific embodiments of the invention described herein.

These and all other equivalents are intended to be encompassed by the following claims.

I claim:

1. A method for extracting collagen from animal collagen-containing tissue, comprising:
   contacting the tissue with a solution of an organic amine salt, under conditions whereby collagen is extracted from animal collagen containing tissue, and said organic amine being selected from the group consisting of diamines and aminoalcohols, and
   recovering collagen extracted from animal collagen-containing tissue into said organic amine salt solution.

2. A method for extracting collagen according to claim 1, wherein the collagen is recovered as a gel.

3. A method for extracting collagen according to claim 1, wherein the collagen is recovered as fibrils.

4. A method for extracting collagen according to claim 1, wherein the collagen is recovered by extrusion.

5. A method for extracting collagen according to claim 1, wherein the organic amine is selected from the group consisting of ethylenediamine, propylenediamine, hexadiamine, and 2-aminoethanol.

6. A method for extracting collagen according to claim 1, wherein the salt is a salt of a strong acid.

7. A method for extracting collagen according to claim 6, wherein the salt of a strong acid is selected from the group consisting of hydrochloride, hydrobromide, and hydrofluoride.

8. A method for extracting collagen according to claim 1, wherein the conditions whereby collagen is extracted from animal collagen-containing tissue is at a pH of about 6.0 to about 9.0.

9. A method for extracting collagen according to claim 1, wherein the conditions whereby collagen is extracted from animal collagen-containing tissue is at a pH of about 7.6 to about 8.2.

10. A method for extracting collagen according to claim 1, wherein the solution of an organic amine salt has a concentration from about 0.3 to about 2.0 moles per liter of solution.

11. A method for extracting collagen according to claim 1, wherein the solution of an organic amine salt has a concentration of about 1.0 moles per liter of solution.

12. A method for extracting collagen according to claim 1, further comprising:
    shearing the animal collagen-containing tissue subsequent to contacting it with the solution of an organic amine salt.

13. A method for extracting collagen according to claim 1, further comprising contacting the animal collagen-containing tissue with a thiol.

14. A method for extracting collagen according to claim 3, wherein the thiol is mercaptoethanol, dithiothreitol, or dithioerythreitol.

15. A method for extracting collagen from animal collagen-containing tissue, comprising:
    contacting the animal collagen-containing tissue with a solution of ethylenediamine hydrochloride at a pH of about 6.0 to about 9.0;
    shearing the animal collagen-containing tissue contacted with the solution of ethylenediamine hydrochloride to form a slurry;
    adding a thiol to said slurry; and
    forming a gel from said slurry.

16. Fibrillar collagen produced by the method of claim 1.

17. Translucent gel collagen produced by the method of claim 1.

18. The method of claim 12, further comprising contacting the animal collagen-containing tissue with a thiol.

19. A method for extracting collagen from animal collagen-containing tissue, comprising:
    (a) contacting the tissue with a solution of an organic amine salt, wherein said organic amine is selected from the group consisting of diamines and amino alcohols and the salt is any salt of a strong acid, thereby producing a mixture;
    (b) extracting out the solubilized collagen from the mixture formed in step (a) by a separation procedure; and
    (c) regenerating the extracted collagen by a regeneration procedure.

20. The method of claim 19, wherein the strong acid is hydrochloric acid.

21. The method of claim 20, wherein the separation procedure is centrifugation followed by dialysis.

22. The method of claim 20, wherein the regeneration procedure is extrusion, casting or molding.

* * * * *

UNITED STATES PATENT AND TRADEMARK OFFICE
CERTIFICATE OF CORRECTION

PATENT NO. : 4,983,721

DATED : January 8, 1991

INVENTOR(S) : Peter F. Davison

It is certified that error appears in the above-identified patent and that said Letters Patent is hereby corrected as shown below:

Column 10, Claim 14, line 20, change "claim 3" to ---claim 13---.

Signed and Sealed this

Nineteenth Day of May, 1992

Attest:

DOUGLAS B. COMER

*Attesting Officer*    *Acting Commissioner of Patents and Trademarks*